(12) United States Patent
Bonstein et al.

(10) Patent No.: US 6,562,297 B1
(45) Date of Patent: May 13, 2003

(54) PH SENSOR FOR INDICATING THE PH OF A SAMPLE

(75) Inventors: Lilach Bonstein, Zichron Yaakov (IL); Amnon Kritzman, Zichron Yaakov (IL)

(73) Assignee: Common Sense Ltd., Nazereth (IL)

( * ) Notice: Subject to any disclaimer, the term of this patent is extended or adjusted under 35 U.S.C. 154(b) by 0 days.

(21) Appl. No.: 09/372,571

(22) Filed: Aug. 12, 1999

(51) Int. Cl.[7] .................................................. A61F 13/15
(52) U.S. Cl. ......................... 422/56; 604/318; 436/163
(58) Field of Search .................... 422/55, 56; 436/163, 436/63; 604/318

(56) References Cited

U.S. PATENT DOCUMENTS

| | | | |
|---|---|---|---|
| 2,664,879 A | 1/1954 | Hardy | |
| 3,509,872 A | 5/1970 | Truhan | |
| 4,029,597 A | 6/1977 | Neisius et al. | |
| 4,029,598 A | 6/1977 | Neisius et al. | |
| 4,666,833 A * | 5/1987 | Roy et al. ..................... | 435/26 |
| 5,063,930 A | 11/1991 | Nucci ......................... | 128/632 |
| 5,094,955 A * | 3/1992 | Calandra et al. ............. | 435/291 |
| 5,217,444 A | 6/1993 | Schoenfeld | |
| 5,275,591 A | 1/1994 | Mavinkurve ................. | 604/389 |
| 5,304,468 A * | 4/1994 | Phillips et al. ................. | 435/14 |
| 5,384,411 A | 1/1995 | Robotti et al. | |
| 5,425,377 A | 6/1995 | Caillouette ................... | 128/759 |
| 5,445,147 A | 8/1995 | Schoendorfer et al. ..... | 128/632 |
| 5,470,752 A * | 11/1995 | Burd et al. .................... | 436/87 |
| 5,823,953 A | 10/1998 | Roskin et al. .............. | 600/367 |
| 5,853,669 A | 12/1998 | Wolfbeis | |
| 5,876,389 A | 3/1999 | Bouchard et al. ......... | 604/385.1 |
| 5,925,318 A * | 7/1999 | Kruzel et al. .................. | 422/56 |
| 6,106,461 A | 8/2000 | Roskin et al. .............. | 600/309 |
| 6,126,597 A | 10/2000 | Smith et al. ................ | 600/362 |
| 6,149,590 A | 11/2000 | Smith et al. ................ | 600/367 |

* cited by examiner

Primary Examiner—Jeffrey Snay
(74) Attorney, Agent, or Firm—Winston & Strawn

(57) ABSTRACT

A pH sensor for the visual or optical indication of the pH of a sample. The pH sensor includes a hydrophilic, optionally intrinsically charged or neutral, synthetic membrane and at least one pH indicator dye immobilized thereto, so as to prevent appreciated bleeding of the at least one indicator dye from the synthetic membrane upon immersion in an aqueous liquid.

21 Claims, 1 Drawing Sheet

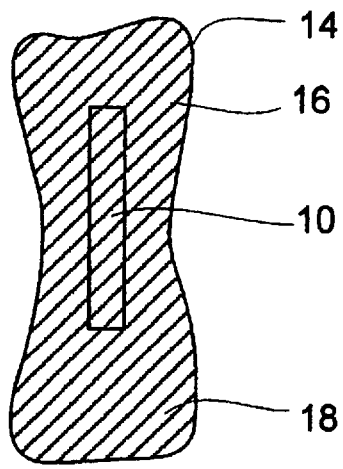
Fig. 1
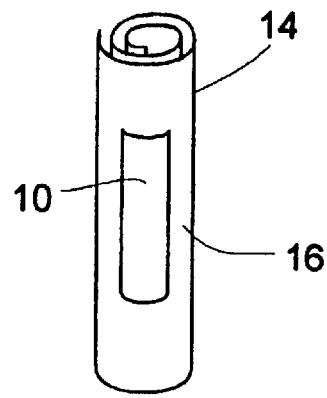
Fig. 2
Fig. 3
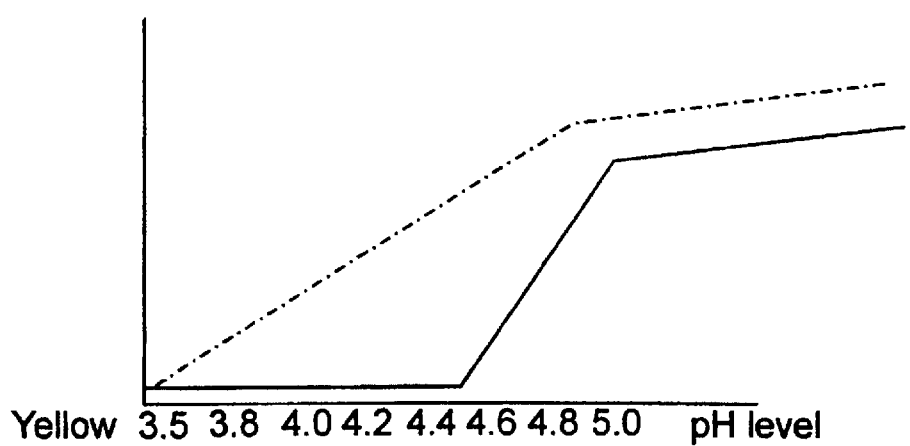
----- Bromocresol Green
——— Bromocresol Green+Methyl Orange 1:4
Fig. 4

PH SENSOR FOR INDICATING THE PH OF A SAMPLE

FIELD AND BACKGROUND OF THE INVENTION

The present invention relates to a pH sensor for the visual or optical indication of the pH of a sample, the sensor having a mechanically stable support and an indicator dye immobilized thereby. The invention further relates to a process for fabricating a pH sensor for visual or optical indication of the pH of a sample, in which a pH indicator dye is immobilized by a mechanically stable support, such that the indicator dye does not appreciatively bleed when contacted with the sample. In addition, the invention also relates to the use of a pH sensor of this type. Finally, the invention also relates to an efficient method of selecting pH indicator dyes and/or dyes ratio for obtaining a pH indicator dye mixture which is sensitive to a subtle change in pH.

The optical measurement of the pH goes back to the finding that certain dyes, (such as, for example, litmus and tea) react to the pH of a sample by changing their color and are thus able to indicate the pH of a sample. A selection of suitable dyes (indicators), together with the pH ranges within which they change color, is found, for example, in "Indicators", E. Bishop, Pergamon Press, 1972, chapter 3, which is incorporated herein by reference.

The first pH-sensitive strip materials were obtained by immersing a paper strip in a dye solution. The dye in color strips of this type is bound to the support by absorption. This has the drawback that the dye can be washed out by the sample, which makes such strips unsuitable for applications wherein indicator contamination is unacceptable and for continuous processes. In addition, in many cases, upon drying such strips loose their pH indicative color.

By means of chemical or physical immobilization of dyes washing out can be prevented. Immobilized pH-sensitive materials are therefore suitable for the continuous measurement of pH and for applications wherein indicator contamination are unacceptable.

An early study of bacterial vaginosis (BV) involved comparisons of the pH of vaginal fluids of women known to be suffering from BV with those known to be free of the disease. Gardner, H. L., et al., Am. J. Obstet. Gynecol. 69:962 (1955). All of the BV positive women in the study were determined to have a vaginal fluid pH greater than 4.5, and 91% of these women had a vaginal fluid pH greater than 5.0. Of the normal (disease-free) women in the test, 92% were found to have vaginal pH between 4.0 and 4.7. The conclusion drawn from the study was that a vaginal pH equal to or greater than 5.0 in conjunction with other clinical criteria was indicative of the presence of BV.

Subsequent studies culminating by Amsel, R., et al., Am. J. Med. 74:14–22 (1983), resulted in a reduction of the pH threshold for BV to 4.5, and established the remaining criteria as vaginal fluid homogeneity, the whiff test (treatment with alkali followed by an olfactory test to detect for an amine odor), and the presence of clue cells. These are commonly referred to as the Amsel clinical criteria for BV. The conclusion was based on a study group of 397 women in which 81% of BV positive women were found to have a pH greater than 4.5 while only 23% of the normal women were found to have a vaginal fluid pH greater than 4.5.

Studies subsequent to the report by Amsel et al. have now adjusted the pH threshold to 4.7. One of these is the study of Holst, E., J. Clin. Microbiol. 28:2035–2039 (1990), in which 100% of the women diagnosed as BV positive by the Amsel criteria were reported to have vaginal fluid pH greater than 4.7. Another is the study by Eschenbach, D. A., Am. J. Obstet. Gynecol. 158(4):819–828 (1988), in which all 257 women in the study group who had at least 20% clue cells were shown to have a vaginal fluid pH greater than or equal to 4.7, leading to the conclusion that a threshold value of 4.7 correlated best with the other clinical evidence of BV. Krohn, M. A., et al., J. Clin. Microbiol. 27(6):1266–1271 (1989), also verified the correlation between the vaginal fluid pH threshold of 4.7 and the presence of clue cells, and Holmes, K. K., and coworkers further confirmed the pH 4.7 threshold as an indicator of BV—Holmes, K. K., et al., eds., Sexually Transmitted Diseases, McGraw-Hill, New York (1990), Chapter 46:527–545 (Holmes, K. K., et al.), and Chapter 47:547–559 (Hillier, S. L., et al.).

Colorimetric tests for elevated vaginal fluid pH have used nitrazine yellow as an indicator. Nitrazine yellow is a monoazo dye that is bright yellow at pH 6.0 and bright blue at pH 7.2, and has a grey-green midpoint at pH 6.6. In the range of interest for testing vaginal fluid, however, which is approximately 3.5 to 6.0, the change occurs in subtle progressions of grey-green that are difficult to interpret.

pH thresholds are useful indicators in diagnosing a variety of other biological conditions, in both humans and animals, and a large number of colorimetric indicators are known and commercially available. Selection of the appropriate indicator is not always a simple task, however, and the choices are often limited, particularly when a specific color change is desired and when stability of the indicator is a consideration.

Normal bovine milk, for example, has a pH of 6.5 to 6.8, and it has been reported (N. Z. J. Sci. Technol. 27:258 (1945)) that bovine milk with a pH greater than 6.8 may indicate the presence of bovine mastitis. The difficulties of detecting a pH deviation of such a small magnitude using conventional paper indicator strips are discussed above.

A study specifically directed to bovine mastitis was reported in J. Dairy Sci. 68: 1263–1269 (1985). The purpose of the study was to determine the suitability of using absorbent blotting paper impregnated with the pH indicator bromthymol blue to test the pH of bovine milk as a method of detecting subclinical bovine mastitis. Milk was added to the indicator-treated paper, and the color of the pH indicator spot was scored on a scale of 1 to 4, where 1 (pale green) was assessed as normal (negative), and 2, 3 and 4 (increasing from moderate green to dark blue-green) were considered abnormal (positive). The pH of the milk was also determined electronically with a carefully calibrated pH meter. The test results illustrated the difficulty in defining accurately the color of the test area: the predictive value of a positive colorimetric test ranged from 49% to 52% (i.e., 51% to 48% of the results were false positives).

As expected, an increase in the test score was accompanied by an increase in the severity of mastitis as defined by other diagnostic measures. However, in milk from animals with less severe mastitis, the considerable overlapping of results highlighted the possible error in interpretation of indicator scores. The wide variation of milk pH as determined electronically within each BTB (Brom Thymol Blue) color score showed that the indicator results were not closely related to pH. The investigators stressed the importance of using color comparators which resemble as closely as possible the actual pH test method being utilized. If the colorimetric milk pH test results were to be interpreted immediately, it was important to use comparators that were also wetted with milk. If the calorimetric pH test results were to be determined after the milk spots had dried, it was advantageous to use dry comparators.

Returning to bacterial vaginosis, the whiff test, which is one of the Amsel criteria, originated in a study by Pheifer, et al., N. Engl. J. Med. 298:1429–1434 (1978), that reported the presence of a characteristic fishy amine odor upon the addition of 10% KOH to a vaginal fluid specimen from a woman with BV. The odor is caused by the alkaline volatilization of amine salts found in the vaginal fluid of women with BV. Unfortunately, the test is highly subjective, it exposes the health care worker to potential biological hazards, and it is disagreeable and vulnerable to error, since it is performed on a microscope slide which, due to the transient nature of the amine odor, must be placed directly under the nose and sniffed immediately after the addition of the KOH.

Alternatives to the whiff test are analytical procedures such as high voltage electrophoresis (Chen, K. C. S., et al., J. Clin. Invest. 63:828–835 (1979)), thin-layer chromatography (Chen, K. C. S., et al., J. Infect. Dis. 145:337–345 (1982), and Sanderson, B. E., et al., Br. J. Vener. Dis. 59:302–305 (1983)), gas chromatography (Gravett, M. G., et al. Obstet. Gynecol. 67:229–237 (1986), and Dravenieks, A., et al., J. Pharma. Sc. 59:495–501 (1970)), and high-performance liquid chromatography (Cook, R. L., et al., J. Clin. Microbiol. 30:870–877 (1992)). These procedures, although more accurate and reliable than the whiff test, are expensive, time-consuming, and not suitable for on-site testing in a physician's office or clinic.

Clue cells, which constitute a further Amsel criterion, are independently correlated with BV, and in the hands of a skilled microscopist are a very sensitive and specific indication of this infection. Clue cells are squamous vaginal epithelial cells found in vaginal fluid when BV is present. The cells are covered with numerous bacteria, giving them a stippled or granular appearance, and their borders are obscured or fuzzy because of the adherence of numerous rods or cocci. According to standard clinical practice, a diagnosis of BV is established when at least 20% of the detectable epithelial cells are clue cells. Holmes, et al., Sexually Transmitted Diseases, 2d ed., McGraw-Hill, Inc., New York, 1990.

Distinguishing between true clue cells in which the adherent bacteria completely obscure the edges of the cells and cells with simply a few adherent bacteria requires training and experience. One source of error is similarity in appearance between clue cells and trichomonads, white blood cells and other vaginal fluid components, frequently resulting in an incorrect identification of these cells as clue cells, and therefore false positive test results. Another is that clue cells when present are frequently obscured by numerous vaginal fluid components causing the clinician to miss the clue cells completely or to quantify them at levels below their actual level. This can result in a false negative test result. Therefore, it would be highly desirable to have a distinct analyte that is accurately and conveniently monitored and whose presence is correlated with clue cells.

U.S. Pat. No. 5,217,444 to Schoenfeld teaches an absorbent pad, for use in absorbing secretions from a person's body, which includes a pH indicator material indicating by a color change the acidity or alkalinity of a liquid coming into contact with it. The pH indicator material is wetted by the secretions absorbed by the pad, and thereby provides an indication of the health condition of the person's body.

U.S. Pat. No. 5,853,669 to Wolfbeis teaches a hydrophilic accommodating layer disposed on a hydrophobic mechanically stable support element, which layer contains an indicator dye proper in an immobilized form for the purpose of visual or optical indication of the pH of a sample which can be used as the pH indicator in the pad of Schoenfeld and in other applications as well.

SUMMARY OF THE INVENTION

One object of the present invention is to improve a pH sensor of the type mentioned in the preamble and a process for fabricating a pH sensor of this type, so as to enable a simple fabrication or even mass production of pH sensors which are inexpensive and thus suitable as an expendable pH sensor.

Another object of the present invention is to provide hygienic pads in which a pH sensor as herein described is incorporated for monitoring a user's health condition.

Still another object of the present invention is to provide an efficient method of selecting pH indicator dyes and/or dyes ratio for obtaining a pH indicator dye mixture which is sensitive to a subtle change in pH.

Thus, according to one aspect of the present invention there is provided a pH sensor for the visual or optical indication of the pH of a sample, the pH sensor comprising a hydrophilic, intrinsically charged or neutral, synthetic membrane and at least one pH indicator dye immobilized thereto, so as to prevent appreciated bleeding of the at least one indicator dye from the synthetic membrane upon immersion in an aqueous liquid.

According to another aspect of the present invention there is provided a method of manufacturing a non-bleeding pH sensor, the method comprising the step of immobilizing at least one pH indicator dye onto a hydrophilic, optionally intrinsically charged or neutral, synthetic membrane, so as to prevent appreciated bleeding of the at least one indicator dye from the synthetic membrane upon immersion in an aqueous liquid.

According to yet another aspect of the present invention there is provided an absorbent body for absorbing vaginal discharge of a person, comprising an absorbent material and a pH sensor being combined therewith for the visual or optical indication of the pH of the vaginal discharge, the pH sensor including a hydrophilic, optionally intrinsically charged or neutral, synthetic membrane and at least one indicator dye immobilized thereto, so as to prevent appreciated bleeding of the at least one indicator dye from the synthetic membrane upon immersion in an aqueous liquid, the pH sensor being included in the absorbent body so as to be wetted by the secretions absorbed by the absorbent material, thereby providing an indication of the health condition of the person's body.

According to still another aspect of the present invention there is provided a method of providing an indication of the health condition of a person's body, the method comprising the steps of (a) collecting vaginal discharge of the person into an absorbent body including an absorbent material and a pH sensor being combined therewith for the visual or optical indication of the pH of the vaginal discharge, the pH sensor including a hydrophilic, optionally intrinsically charged or neutral, synthetic membrane and at least one indicator dye immobilized thereto, so as to prevent appreciated bleeding of the at least one indicator dye from the synthetic membrane upon immersion in an aqueous liquid, the pH sensor being included in the absorbent body so as to be wetted by the secretions absorbed by the absorbent material; and (b) optically inspecting the pH sensor for a color change, thereby providing an indication of the health condition of the person's body.

According to a further aspect of the present invention there is provided a method of producing an absorbent body for absorbing vaginal discharge of a person and for providing an indication of the health condition of the person's body, the method comprising the step of combining an absorbent material and a pH sensor, the pH sensor being for the visual or optical indication of the pH of the vaginal discharge, the pH sensor including a hydrophilic, optionally intrinsically charged or neutral, synthetic membrane and at least one indicator dye immobilized thereto, so as to prevent appreciated bleeding of the at least one indicator dye from the synthetic membrane upon immersion in an aqueous liquid, the pH sensor being included in the absorbent body so as to be wetted by the secretions absorbed by the absorbent material, thereby providing an indication of the health condition of the person's body.

According to further features in preferred embodiments of the invention described below, the at least one pH indicator dye is sensitive to a subtle change in pH of less than N pH units, wherein N is selected from the group consisting of 0.5 pH units, 0.4 pH units, 0.3 pH units, 0.2 pH units and 0.1 pH units.

According to still further features in the described preferred embodiments the hydrophilic synthetic membrane is positively charged.

According to still further features in the described preferred embodiments the hydrophilic synthetic membrane is negatively charged.

According to still further features in the described preferred embodiments the hydrophilic synthetic membrane is amphoteric.

According to still further features in the described preferred embodiments the hydrophilic synthetic membrane is a Nylon membrane.

According to still further features in the described preferred embodiments the Nylon is Nylon 6.6.

According to still further features in the described preferred embodiments hydrophilic synthetic membrane is a polyamide membrane.

According to still, further features in the described preferred embodiments hydrophilic synthetic membrane is an arylamide membrane.

According to still further features in the described preferred embodiments the at least one pH indicator dye produces a color change at a pH of between pH value of 4.0 and 5.0.

According to an additional aspect of the present invention there is provided a method of selecting pH indicator dyes and dyes ratio for obtaining a pH indicator dye mixture which is sensitive to a subtle change in pH, the method comprising the steps of (a) providing a plurality of transparent containers; (b) dividing the plurality of transparent containers into pH groups by filling containers of each of the pH groups with a buffered solution of a predetermined pH value; (c) introducing into each of the plurality of containers a single pH indicator dye of a known concentration, such that different containers of a single group of containers include different pH indicator dyes and optionally different concentrations of a specific pH indicator dye; (d) selecting at least two containers of a specific pH group, each of the at least two containers including a different pH indicator dye and positioning the at least two containers against a light source so as to optically monitor a color obtained by combining color contributions of each of the at least two containers; and (d) optionally repeating step (d) with containers of one or more of the pH groups until identifying pH indicator dyes and/or dyes ratio, such that when mixed to form the pH indicator dye mixture will be sensitive to the subtle change in pH.

According to further features in preferred embodiments of the invention described below, the subtle change in pH is of less than N pH units, wherein N is selected from the group consisting of 0.5 pH units, 0.4 pH units, 0.3 pH units, 0.2 pH units and 0.1 pH units.

The present invention successfully addresses the shortcomings of the presently known configurations by providing a pH sensor for the visual or optical indication of the pH of a sample, an method of manufacturing same, an absorbent body for absorbing vaginal discharge of a person including same, a method of providing an indication of the health condition of a person's body using same, a method of producing an absorbent body for absorbing vaginal discharge of a person and for providing an indication of the health condition of the person's body and a method of selecting pH indicator dyes and dyes ratio for obtaining a pH indicator dye mixture which is sensitive to a subtle change in pH.

BRIEF DESCRIPTION OF THE DRAWINGS

The invention is herein described, by way of example only, with reference to the accompanying drawings, wherein:

FIG. 1 is a top view of a pH sensor according to the present invention;

FIG. 2 is a top view of a hygienic pad including the pH sensor according to the present invention;

FIG. 3 is a perspective view of a tampon including the pH sensor according to the present invention; and FIG. 4 is a graph showing the change in color as a function of pH for 0.1% Bromocresol Green as is compared with a mixture of 1 volume of Bromocresol Green mixed with 3 volumes of 0.1% Methyl Orange.

DESCRIPTION OF THE PREFERRED EMBODIMENTS

The present invention is of a pH sensor for the visual or optical indication of the pH of a sample which can be used in an absorbent body for absorbing vaginal discharge of a person. Specifically the present invention can be used to provide an indication of the health condition of a person's body. The present invention is further of a method of manufacturing a pH sensor for the visual or optical indication of the pH of a sample, a method of producing an absorbent body for absorbing vaginal discharge of a person and for providing an indication of the health condition of the person's body and a method of selecting pH indicator dyes and/or dyes ratio for obtaining a pH indicator dye mixture which is sensitive to a subtle change in pH.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As shown in FIG. 1, according to one aspect of the present invention there is provided a pH sensor 10 for the visual or optical indication of the pH of a sample. pH sensor 10 includes a hydrophilic, optionally intrinsically charged or neutral, synthetic membrane and at least one pH indicator dye immobilized thereto, so as to prevent appreciated bleeding of the at least one indicator dye from the synthetic membrane upon immersion in an aqueous liquid.

As used herein in the specification and in the claims section that follows, the phrase "a hydrophilic, optionally intrinsically charged or neutral, synthetic membrane" refers to non-natural membranes which are positively charged, such as the BIODYNE B/PLUS membrane by PALL Gelman Laboratory, membranes which are negatively charged, such as the BIODYNE C membrane by PALL Gelman Laboratory, membranes which are amphoteric, such as the BIODYNE A membrane by PALL Gelman Laboratory. Such a synthetic membrane can be made of any suitable synthetic polymer, such as, but not limited to polyamide (Nylon, e.g., Nylon 6.6) and arylamide. Synthetic membranes are presently preferred over fibrous natural membranes such as nitrocellulose based membranes because it was experimentally determined that (i) such membranes better maintain their structural integrity under wider pH ranges as is compared with natural membranes such as cellulose or nitrocellulose based membranes; and (ii) such membranes readily immobilize a plurality of pH indicator dyes.

As used herein in the specification and in the claims section that follows, the phrase "at least one pH indicator dye" refers to a single pH indicator dye or a mixture of at least two different pH indicator dyes, wherein in different mixtures each of the at least one pH indicator dye may be present in a different concentration.

As used herein in the specification and in the claims section that follows, the phrase "appreciated bleeding" refers to eye detectable leakage of the at least one pH indicator dye into an aqueous liquid, such as a buffer solution, in a predetermined pH range, e.g., of 2 pH units, through which color change of the pH indicator dye is experienced, over a predetermined time period, e.g., 24 hours, at a temperature between e.g., 22° C. and 37° C. The phrase also refers to eye detectable leakage of the at least one pH indicator dye onto a wet white fibrous material.

According to another aspect of the present invention there is provided a method of manufacturing a non-bleeding pH sensor. The method according to this aspect of the present invention is effected by immobilizing at least one pH indicator dye onto a hydrophilic, optionally intrinsically charged or neutral, synthetic membrane, so as to prevent appreciated bleeding of the at least one indicator dye from the synthetic membrane upon immersion in an aqueous liquid. Immobilization according to this aspect of the present invention can be effected by immersing the membrane in an aqueous solution of the at least one pH indicator in an appropriate concentration, ranging between 0.01 w/v % and 1 w/v % for several hours, e.g., at least 4 hours, preferably at least 6 hours, more preferably at least 10 hours, still more preferably at least 15 or 20 hours, followed by washing the membrane in a wash solution and immobilizing the at least one pH indicator dye thereto by an immobilization method, such as, but not limited to, placing the membrane over an absorbing material and drying the membrane under low humidity conditions (e.g., not more than 30% air humidity) at, for example, room temperature, for several hours. It was experimentally determined that using the above protocol, a variety of pH indicator dyes were immobilized to an amphoteric Nylon membrane and showed no appreciated bleeding thereafter.

A unique feature of the protocol herein described is the stability of the color change of pH sensor 10. Thus, while prior art pH strips change color, the color is maintained thereby as long as the strip is kept humid, however, the color fades upon drying. While practicing the above protocol, the inventors were surprised to find out that for a plurality of pH indicators tested, the color change developed following pH change remained substantially, unchanged and in some cases became more pronounced after drying. For example, by mixing 1 volume of 0.1% Bromocresol Green with 3 volumes of Methyl Orange and immobilizing the pH indicator dyes mixture onto an amphoteric Nylon membrane as herein described a pH sensor was obtained which was lemonish at pHs 4.2 and 4.4 and turned bluish-green at pH 4.6. The bluish-green color was maintained substantially unchanged also after drying the membrane and keeping it dry for over two weeks.

According to a preferred embodiment, both the aqueous solution and the wash solution are either a buffered solution or a non-buffered solution, respectively, having a pH value in a range of less than ±0.5–1.0 pH units of the pH value inducing a color change on the at least one pH indicator.

Thus, the present invention provides an assay for pairing appropriate membranes with appropriate pH indicator dyes. According to this assay, any one of the above described membranes is tested for appreciated bleeding following the immobilization protocol as herein described. This assay can be rendered more sensitive by spectroscopically monitoring the bleeding to thereby determine bleeding, if any.

As shown in FIGS. 2–3, according to yet another aspect of the present invention there is provided an absorbent body 14 for absorbing vaginal discharge of a person. Absorbent body 14 includes an absorbent material 16 which, as shown in FIG. 2, can be arranged in a flattened layers configuration, such a hygienic pad, or, as specifically shown in FIG. 3, rolled or folded into a compact configuration, such as a tampon. In any case, absorbent body 14 further includes a pH sensor, such as pH sensor 10 as described hereinabove, which is combined with material 16 for the visual or optical indication of the pH of the vaginal discharge. Thus, pH sensor 10 is included in absorbent body 14 so as to be wetted by the secretions absorbed by absorbent material 16, thereby to provide an indication of the health condition of the person's body, as is further detailed in the background section above and in U.S. Pat. No. 5,217,444 to Schoenfeld and U.S. Pat. No. 5,853,669 to Wolfbeis both are incorporated by reference as if fully set forth herein. pH sensor 10 can be located at any location with respect to, for example, pad 14 of FIG. 2. It is preferably centered. It can be located at either side of pad 14. Similarly, pH sensor 10 can be located at any location with respect to, for example, tampon 14 of FIG. 3. It is preferably centered. In both cases, pH sensor 10 can be either externally attached to material 16 body 14 or internally embedded between layers of material 16. Material 16 can be any absorbent substance, including, but not limited to, natural fibers, such as cotton fibers, or a gelating substance, as well known in the art. Additional layers, such as an external protective, water impermeable, layer 18 can be employed, as well known in the art. Such a protective layer 18 is preferably selected transparent, so as to enable a user to view pH sensor 10 and any color change thereof therethrough.

According to still another aspect of the present invention there is provided a method of providing an indication of the health condition of a person's body. The method according to this aspect of the present invention is effected by collecting vaginal discharge of the person into an absorbent body such as absorbent body 14 described hereinabove and optically inspecting, e.g., by a colorimeter or by eye inspection, the pH sensor for a color change, thereby providing an indication of the health condition of the person's body in relation to bacterial vaginosis, all as further detailed in the background section above.

According to a further aspect of the present invention there is provided a method of producing an absorbent body for absorbing vaginal discharge of a person and for providing an indication of the health condition of the person's body. The method according to this aspect of the present invention is effected by combining an absorbent material and a pH sensor as further detailed hereinabove.

As is further detailed in the background section above subtle pH changes are in some cases indicative of a pathological state. Therefore, according to a preferred embodiment of the present invention, the at least one pH indicator dye is selected sensitive to a subtle change in pH, such as, but not limited to, less than 0.5 pH units, less than 0.4 pH units, less than 0.3 pH units, less than 0.2 pH units or less than 0.1 pH units. The sensitivity should be tailored to the application. Thus, for diagnosis of bacterial vaginosis pH change of about 0.4 pH units is of choice. In this case, the at least one pH indicator dye produces a color change at a pH of between pH value of 4.0 and 5.0, preferably between pH value of 4.2 and 4.6.

According to an additional aspect of the present invention there is provided a method of selecting pH indicator dye combinations and dyes ratio(s) for obtaining a pH indicator dye mixture which is sensitive to a subtle change in pH. The method according to this aspect of the present invention is effected by implementing the following method steps, in which, in a first step, a plurality of transparent containers are provided. The containers are preferably cubic containers, such as quvettes, e.g., quartz or glass quvettes. In a second step of the method according to this aspect of the present invention the plurality of transparent containers are divided into pH groups by filling containers of each of the pH groups with a buffered solution of a predetermined pH value. Containers of different pH groups are filled with buffers which differ by subtle pH values, such as less than 0.5 pH units, less than 0.4 pH units, less than 0.3 pH units, less than 0.2 pH units, less than 0.1 pH units or for some applications less than 0.05 pH units, and the groups cover a suitable pH range of e.g., about 1.0 pH unit, say between pH 4.0 and pH 5.0. Then, into each of the plurality of containers a single pH indicator dye of a known concentration is introduced, such that different containers of a single group of containers include different pH indicator dyes and optionally different concentrations of a specific pH indicator dye. Thereafter, at least two containers of a specific pH group are selected. Each of the at least two containers include a different pH indicator dye. The selected containers are positioned against a light source, such as a white light source, so as to optically monitor by a colorimeter (e.g., spectrophotometer) or by eye inspection, a color obtained by combining color contributions of each of the at least two containers so positioned. Finally, the former step is repeated with containers of one or more of the pH groups until pH indicator dyes combination and/or dyes ratio(s) is obtained, such that when mixed to form the pH indicator dye mixture, that mixture will be sensitive to the subtle change in pH in the specified pH range.

This method was practiced in order to combine pairs of pH indicator dies in order to obtain an indicator dye mixture which changes its color when shifting the pH from pH 4.4 to pH 4.6. As further detailed in the background section above, such a pH indicator is useful in the diagnosis of bacterial vaginosis. Table 1 below summarizes the results.

TABLE 1

| 1st pH indicator dye | 1st pH indicator dye | V.R. | Color change |
| --- | --- | --- | --- |
| Bromocresol Green | Methyl Orange | 1/4 | Lemon → Bluish green |
| Mixed indicator 4.5 | Mix 3046 | 1/1 | Pink → Blue |
| Mixed indicator 4.5 | Bromocresol Green | 1/1 | Brown → Blue |
| Congo red | Bromocresol Green | 1/1 and 2/1 | Brown → Blue |
| Bromochlorophenol Blue | Bromocresol Green | 1/2 | Grey → Violet |

V.R. = volume ratio employed. All pH indicator dyes were employed at a concentration of 1 w/v % in water or water mixed with some ethanol. Bromocresol Green (3', 3", 5', 5" tertrabromo-m-cresolsulfonephtalalein, Sigma B-7396); Methyl Orange (Acid orange 52, Sigma M-0402); Mixed indicator 4.5 (Merck 1.0B59.0250); Mix 3046 (BDH 21038 4A); Congo red (Aldrich Chem. 86,095-6); Bromochlorophenol Blue (Sigma B-5008)

FIG. 4 is a graph demonstrating the color change using a mixture of two indicators as compared to a single indicator. Thus, 0.1% Bromocresol Green gradually changes color from yellow to bluish green from pH 3.5 to pH 4.7, after which no substantial further color change is monitorable. In sharp contrast, by mixing 1 volume of 0.1% Bromocresol Green with 3 volumes of Methyl Orange a pH indicator dye mixture is obtained which is lemonish at pHs 3.5 to 4.5 and step wise changes to a bluish-green color at pH 4.5.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A vaginal secretion monitoring article for providing an indication of a person's health, comprising:
   a body that includes an absorbent material for absorbing vaginal secretions; and
   a pH sensor associated with the body for determining pH of the vaginal secretions, the sensor including a positively charged hydrophilic nylon membrane and at least one indicator dye immobilized thereto so as to prevent appreciated bleeding of the dye from the membrane upon immersion in an aqueous liquid, with the sensor being positioned with respect to the body so as to be wetted by the secretions absorbed by the absorbent material;
   wherein the indicator dye changes color to correspond to the pH of the vaginal secretions and the positively charged hydrophilic nylon membrane prevents the color change from fading after drying of the membrane, thereby providing a reliable indication of the health of the person.

2. The article of claim 1 wherein the at least one indicator dye is sensitive to a subtle change in pH of less than N pH units, wherein N is selected from the group consisting of 0.5, 0.4, 0.3, 0.2, 0.1 and 0.05 pH units.

3. The article of claim 1 wherein the dye produces a color change at a pH of between 4 and 5.

4. The article of claim 1 wherein the color of the indicator dye is enhanced after drying of the membrane.

5. The article of claim 1 wherein the pH sensor is externally attached to the body, wherein the body includes a transparent, water-impermeable layer.

6. The article of claim 1 wherein the pH sensor is imbedded between layers of the absorbent material.

7. The article of claim 1 in the form of a hygienic pad or a tampon.

8. The article of claim 1 wherein at least two pH indicator dyes are immobilized onto the membrane.

9. The article of claim 8 wherein the dyes are present as a dye mixture which more accurately measures the pH of the secretions.

10. A vaginal secretion monitoring article for providing an indication of a person's health, comprising:
    a body that includes an absorbent material for absorbing vaginal secretions; and
    a pH sensor associated with the body for determining pH of the vaginal secretions, the sensor including a positively charged hydrophilic nylon membrane and a mixture of at least two indicator dyes immobilized thereto so as to prevent appreciated bleeding of the dye from the membrane upon immersion in an aqueous liquid, with the sensor being positioned with respect to the body so as to be wetted by the secretions absorbed by the absorbent material;
    wherein the indicator dye mixture is sensitive to a subtle change in pH of 0.1 pH units or less and changes color to correspond to the pH of the vaginal secretions and the positively charged hydrophilic nylon membrane prevents the color change from fading after drying of the membrane, thereby providing a reliable indication of the health of the person.

11. A method of producing a vaginal secretion monitoring article for providing an indication of a person's health, which comprises:
    preparing a pH sensor includes a positively charged hydrophilic nylon membrane and at least one indicator dye for determining pH of the vaginal secretions,
    immobilizing the dye onto the membrane so as to prevent appreciated bleeding of the dye from the membrane upon immersion in an aqueous liquid; and
    associating the sensor with a body that includes an absorbent material for absorbing vaginal secretions, with the sensor being positioned with respect to the body so as to be wetted by the secretions absorbed by the absorbent material;
    wherein the indicator dye changes color to correspond to the pH of the vaginal secretions and the positively charged hydrophilic nylon membrane prevents the color change from fading after drying of the membrane, thereby providing a reliable indication of the health of the person.

12. The method of claim 11 which further comprises selecting the at least one indicator dye to be one that is sensitive to a subtle change in pH of less than N pH units, wherein N is selected from the group consisting of 0.5, 0.4, 0.3, 0.2, 0.1 and 0.05 pH units.

13. The method of claim 11 wherein the dye produces a color change at a pH of between 4 and 5.

14. The method of claim 11 wherein the color of the indicator dye is enhanced after drying of the membrane.

15. The method of claim 11 which further comprises externally attaching the pH sensor to the body and providing the body with a transparent, water-impermeable layer.

16. The method of claim 11 which further comprises providing layers of the absorbent material and imbedding the pH sensor between the layers of absorbent material.

17. The method of claim 11 wherein the sensor and body are provided in the form of a hygienic pad or a tampon.

18. The method of claim 11 wherein at least two pH indicator dyes are immobilized onto the membrane.

19. The method of claim 18 wherein the dyes are provided in a dye mixture that is sensitive to a subtle change in pH.

20. The method of claim 19 wherein the dye mixture is provided by:
    providing a plurality of buffered solutions of predetermined pH values;
    introducing a single, known pH indicator dye into each solution so that the solutions include different pH indicator dyes and optionally different concentrations of the specific pH indicator dyes;
    combining at least two solutions that contain different pH indicator dyes to obtain a color;
    optically monitoring the color of the combined solution; and
    repeating the combining and optically monitoring steps until the resultant solution includes a dye mixture that is sensitive to the subtle change in pH of the vaginal secretions.

21. The method of claim 20 wherein the subtle change in pH is less than N pH units, wherein N is selected from the group consisting of 0.5, 0.4, 0.3, 0.2, 0.1 and 0.05 pH units.

* * * * *

UNITED STATES PATENT AND TRADEMARK OFFICE
CERTIFICATE OF CORRECTION

PATENT NO.     : 6,562,297 B1
DATED          : May 13, 2003
INVENTOR(S)    : Bonstein et al.

It is certified that error appears in the above-identified patent and that said Letters Patent is hereby corrected as shown below:

<u>Title page,</u>
Item [73], Assignee, change "Nazereth" to -- Nazereth Illit --.

Signed and Sealed this

Second Day of September, 2003

JAMES E. ROGAN
*Director of the United States Patent and Trademark Office*